(12) United States Patent
Hart (10) Patent No.: US 8,906,060 B2
(45) Date of Patent: Dec. 9, 2014

(54) METHOD AND APPARATUS FOR SOFT TISSUE FIXATION TO BONE

(75) Inventor: Rickey Hart, Marco Island, FL (US)

(73) Assignee: Karl Storz GmbH & Co. KG, Stamford ( * ) Notice: Subject to any disclaimer, the term of this patent is extended or adjusted under 35 U.S.C. 154(b) by 996 days.

(21) Appl. No.: 12/491,037

(22) Filed: Jun. 24, 2009

(65) Prior Publication Data

US 2010/0331881 A1  Dec. 30, 2010

(51) Int. Cl.
*A61B 17/04* (2006.01)

(52) U.S. Cl.
CPC ..... *A61B 17/0401* (2013.01); *A61B 2017/0409* (2013.01); *A61B 2017/0414* (2013.01); *A61B 2017/0432* (2013.01)
USPC .......................................... 606/232; 606/300

(58) Field of Classification Search
USPC ......... 606/139, 144, 232, 300, 301, 307, 313, 606/314, 286, 319, 104; 623/13.14; 411/325, 33, 44, 54–60.2
See application file for complete search history.

(56) References Cited

U.S. PATENT DOCUMENTS

| | | |
|---|---|---|
| 3,708,883 A | 1/1973 | Flander |
| 4,760,843 A | 8/1988 | Fischer et al. |
| 4,790,304 A | 12/1988 | Rosenberg |
| 5,209,753 A | 5/1993 | Biedermann et al. |
| 5,480,403 A | 1/1996 | Lee et al. |
| 5,601,558 A | 2/1997 | Torrie et al. |
| 5,643,321 A | 7/1997 | McDevitt |
| 5,645,589 A | 7/1997 | Li |
| 5,797,963 A | 8/1998 | McDevitt |
| 5,814,071 A * | 9/1998 | McDevitt et al. ............. 606/232 |
| 7,074,203 B1 | 7/2006 | Johanson et al. |
| 7,201,754 B2 | 4/2007 | Stewart et al. |
| 7,431,735 B2 | 10/2008 | Liu et al. |
| 2003/0153921 A1* | 8/2003 | Stewart et al. .................. 606/72 |
| 2003/0187444 A1* | 10/2003 | Overaker et al. ............... 606/72 |
| 2004/0249466 A1* | 12/2004 | Liu et al. .................... 623/17.16 |
| 2007/0038221 A1 | 2/2007 | Fine et al. |

* cited by examiner

*Primary Examiner* — Katherine M Shi
(74) *Attorney, Agent, or Firm* — St. Onge Steward Johnston & Reens LLC (57) ABSTRACT

A bone anchor having a rivet having a proximal end and a head distal to an elongate body, a sleeve having an internal channel for slidably receiving the body, and an expansion nut having a channel therethrough for slidably receiving said body, proximal of said sleeve is provided. The sleeve further has a shoulder provided within the internal channel in the region of the proximal end for engaging the expansion nut. The rivet, sleeve and expansion nut are arranged such that movement of the rivet from a first position to a second position causes the sleeve to cam over the rivet head and expansion nut until said expansion nut engages said shoulder, forcing the sleeve to expand into a wall of a bone hole.

45 Claims, 10 Drawing Sheets

METHOD AND APPARATUS FOR SOFT TISSUE FIXATION TO BONE

FIELD OF THE INVENTION

The invention relates to anchoring devices and, in particular, to bone anchors for attaching tissue to bone and a method for using the same.

BACKGROUND OF THE INVENTION

In the medical and surgical fields, it is sometimes necessary to perform procedures to reattach soft tissue to bone. Soft tissue, such as a tendon or ligament, may rupture, become damaged, or detach from a patient's bone as a result of injury or a medical procedure. One common type of such injury is a torn rotator cuff. Surgical treatment of a torn rotator is designed to reattach the damaged tendon(s) back to the humeral head (ball of the shoulder joint) from where it is torn.

Bone anchors are one medical implant than can be used to attach soft-tissue to the bone. These anchors are designed to hold the tissue onto the bone at its point of reattachment to allow the tissue to heal and naturally reattach itself to the bone. Typically, the anchor is implanted into a bore or tunnel predrilled into a bone mass and the tendon or ligament is reconnected to the bone with a suture that is attached to the anchor. With advances in arthroscopic surgery, the use of suture anchors has become more popular because of the ease and speed of their use and because of the decreased surgical exposure and morbidity.

Various types of bone anchors are known in the art. For Example, U.S. Pat. No. 5,645,589 to Li teaches a bone anchor having two sections, each having a group of fingers which interdigitate with the fingers of the other section at the midsection of the device. In operation, the sections are inserted into a bone bore and are pressed together, causing the fingers of one or both of the sections to cross and fan outwards and press into the surrounding bone.

U.S. Pat. No. 5,643,321 to McDevitt teaches a bone anchor comprising an expandable sleeve having at least one slit at one end thereof and an expansion member, i.e. rivet, screw, or nut. In operation, the expansion member is forced into the sleeve causing the slits to open and at least one portion of the sleeve to expand and press into the bone hole. Because the slits are only at one end of the sleeve, the sleeve only expands at one end inside the bone hole.

While advancements have been made to bone anchors since their development, these anchors can be tedious to implant and are still prone to dislodgement. Pullout of the anchor commonly causes the tendon or ligament to retear and, while less common, can cause damage to the surrounding bone. Thus, it is desirable to have a bone anchor that can be easily implanted, yet is firmly lodged within the bone hole to resist pull-out.

SUMMARY OF THE INVENTION

Accordingly, it is an object of the present invention to provide a suture anchor that is of simple configuration and is easy to implant into a bone tunnel. It is a further object of the present invention to provide a suture anchor that is resistant to pull-out.

These and other objectives are achieved by providing a bone anchor comprising a rivet having a proximal end and a head distal to an elongate body, a sleeve having an internal channel for slidably receiving the body, and an expansion nut having a channel therethrough for slidably receiving said body, proximal of said sleeve. The sleeve further has a shoulder provided within the internal channel in the region of the proximal end for engaging the expansion nut. The rivet, sleeve and expansion nut are arranged such that movement of the rivet from a first position to a second position causes the sleeve to cam over the rivet head and expansion nut until said expansion nut engages the shoulder, forcing the sleeve to expand into a wall of a bone hole.

In some embodiments, the sleeve further comprises a plurality of axial slits in communication with the internal channel of the sleeve and defining a plurality of flexible wall sections. The plurality of axial slits may comprise at least one axial slit at a proximal end, at least one axial slit at a distal end of the sleeve. In other embodiments, the plurality of axial slits comprises at least two axial slits at the proximal end and at least two axial slits at the distal end.

In other embodiments, the inner surface of the sleeve further comprises a distal camming surface for mating with the rivet head and a proximal camming surface for mating with the expansion nut. The proximal camming surface terminates in the shoulder. The sleeve distal camming surface may be arranged to telescope over the rivet head and the sleeve proximal camming surface may be arranged to telescope over the expansion nut so that when the rivet is moved from a first position to a second position, the plurality of flexible wall sections of the sleeve expand into a wall of a bone hole.

In further embodiments, the expansion nut has a proximal end and a tapered distal end. The proximal camming surface may taper inwards toward the distal end of the sleeve. The distal camming surface may also taper inwards toward the proximal end of the sleeve.

In still further embodiments, the body comprises an eyelet for accommodating a suture. The bone anchor may be made from a bioabsorbable material.

Other objects of the present invention are achieved by provision of a bone anchor comprising a rivet having a proximal end and a head distal to an elongate body, a hollow sleeve, having at least one axial slit at a proximal end, at least one axial slit at a distal end, and an inner surface, the body being at least partially slidably received within the sleeve proximal of the head, and an expansion nut slidably received on the body, proximal of the sleeve. The sleeve also has a shoulder provided on the inner surface in the region of the proximal end for engaging the expansion nut.

Other objects of the present invention are achieved by provision of a method for securing a bone anchor in a bone tunnel comprising the steps of: providing a tunnel in a bone; placing a bone anchor in the tunnel, the bone anchor comprising a rivet having a proximal end and a head distal to an elongate body, a hollow sleeve adapted to receive said body, having a proximal end, a distal end, and an inner surface, and an expansion nut slidably received on said body, proximal of said sleeve, the sleeve further having at least one axial slit at the proximal end, at least one axial slit at the distal end, and a shoulder provided on the inner surface in the region of the proximal end for engaging the expansion nut; moving either the rivet in a proximal direction or the expansion nut in a distal direction so that the sleeve cams over the rivet head and expansion nut until the expansion nut rests on the distal side of the shoulder and causes the sleeve to expand into the bone tunnel at the at least one axial slit at the proximal end and the at least one axial slit at the distal end.

Other objects of the present invention are achieved by provision of a bone anchor comprising a rivet having a proximal end and a head distal to an elongate body, a sleeve having an internal channel for slidably receiving the body, and an expansion nut having a channel therethrough for slidably receiving said body, the sleeve further having a shoulder provided within the internal channel in the region of the proximal end for engaging the expansion nut. The sleeve is disposed proximally of the rivet head and the expansion nut is disposed distally of the sleeve along the body such that movement of the rivet from a first position to a second position causes the sleeve to cam over the rivet head and expansion nut until the expansion nut engages the shoulder, forcing the sleeve to expand into a wall of a bone hole.

Still other objects of the present invention are achieved by providing a rivet having a proximal end and a head distal to an elongate body having two elongate grooves, a hollow sleeve, having at least one axial slit at a proximal end, at least one axial slit at a distal end, and an inner surface, and an expansion nut slidably received on said body, proximal of said sleeve. The body is at least partially slidably received within said sleeve proximal of said head. The head further has a slot for accommodating a suture. In some embodiments, the two elongate grooves are provided in line with the slot.

DETAILED DESCRIPTION OF THE INVENTION

Figure 1:
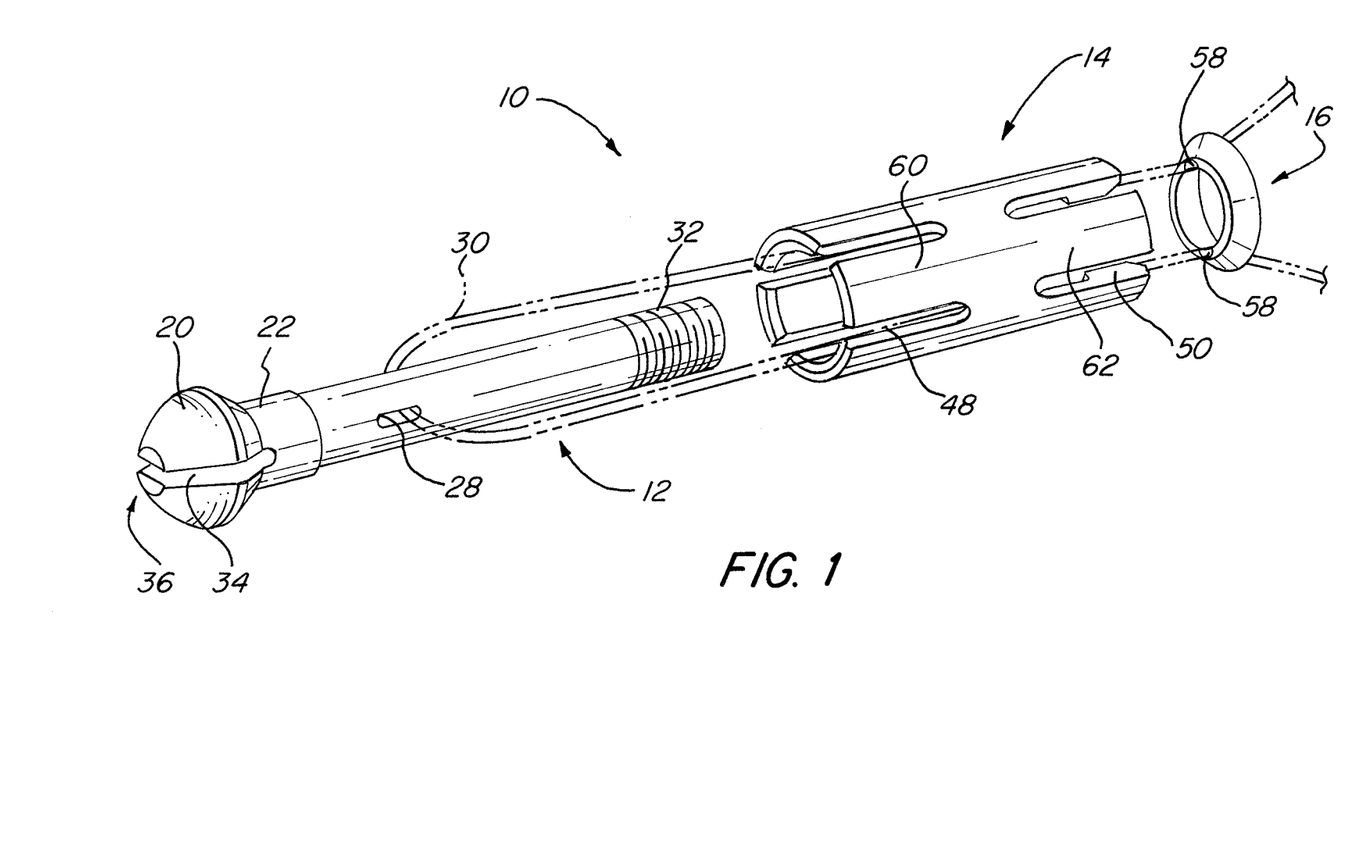
FIG. 1 is an exploded perspective view of one embodiment of the bone anchor of the present invention.
Figure 2A:
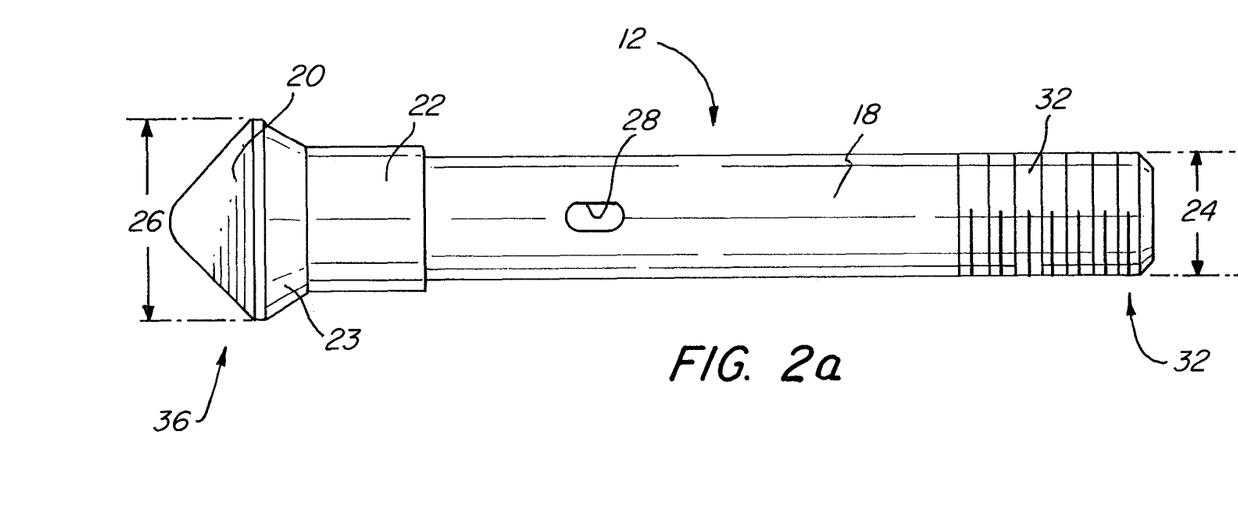
FIG. 2a is a side view of one embodiment of the rivet for use with the bone anchor of the present invention.
Figure 2B:
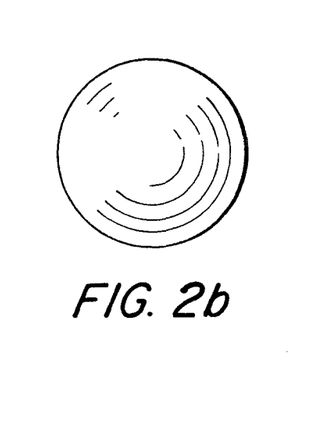
FIG. 2b is a front view of the distal end of one embodiment of the rivet for use with the bone anchor of the present invention.
Figure 2C:
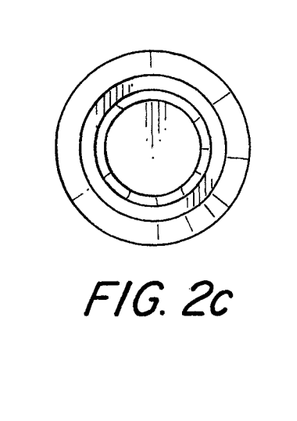
FIG. 2c is a front view of the proximal end of one embodiment of the rivet for use with the bone anchor of the present invention.
Figure 3A:
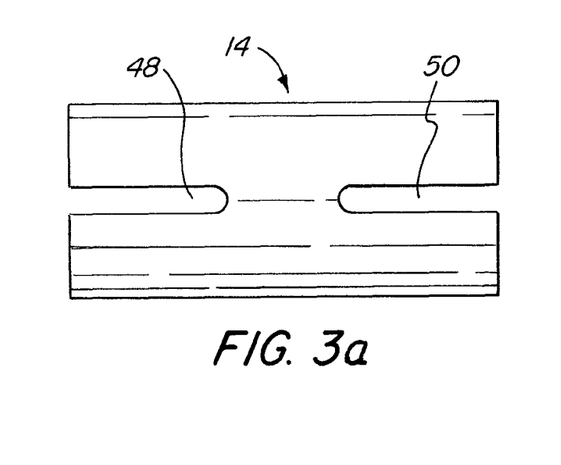
FIG. 3a is a side view of one embodiment of the sleeve for use with the bone anchor of the present invention.
Figure 3B:
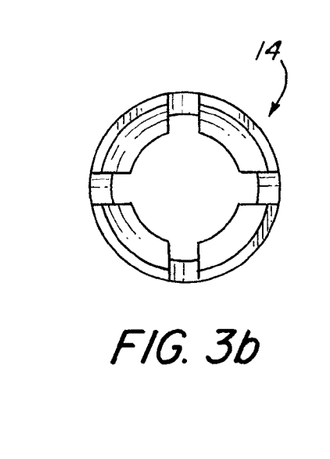
FIG. 3b is a front view of the proximal end of one embodiment of the sleeve for use with the bone anchor of the present invention.
Figure 3C:
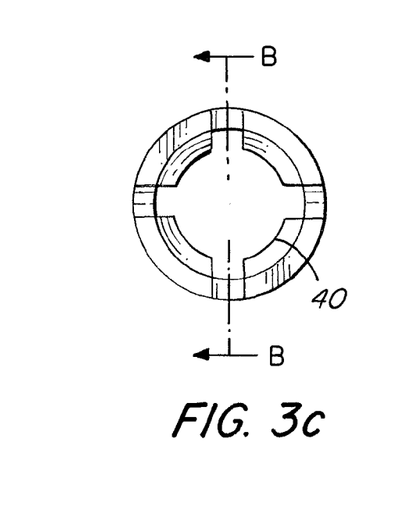
FIG. 3c is a front view of the distal end of one embodiment of the sleeve for use with the bone anchor of the present invention.
Figure 3D:
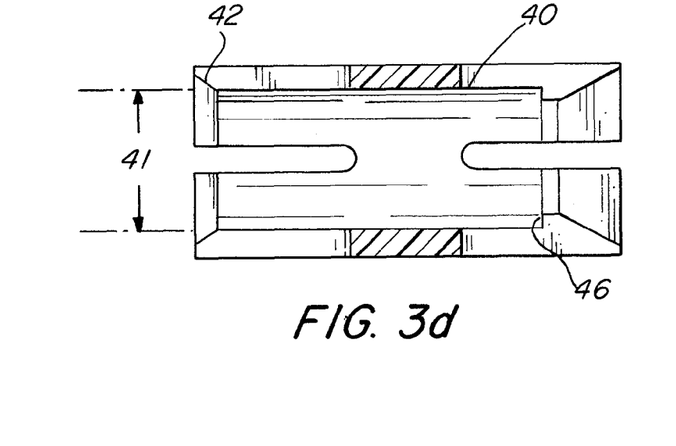
FIG. 3d is a cross sectional view along line B-B of FIG. 3c of one embodiment of the sleeve for use with the bone anchor of the present invention.

With reference now to the figures, one embodiment of the bone anchor 10 is shown. The bone anchor 10 comprises three main components: a rivet 12, a hollow sleeve 14 and an expansion nut 16. In preferred embodiments, these components are fabricated from a bioabsorbable material or a high-strength plastic such as polyetheretherketone (PEEK). As shown in FIGS. 2a-2c, rivet 12 has an elongate body 18, a head 20, and a collar 22, both disposed at the distal end 36 the body. Preferably, the proximal edge 23 of head 20 is tapered to facilitate insertion into the sleeve 14. Body 18 has a diameter 24, which is smaller than the maximum diameter 26 of the head 20. An eyelet 28 is disposed along the body 18 for receiving a suture 30. Rivet 12 may also be provided with threads 32 at its proximal end 38 and a slot 34 at its distal end 36 for being screwed into a loading gun.

Figure 7:
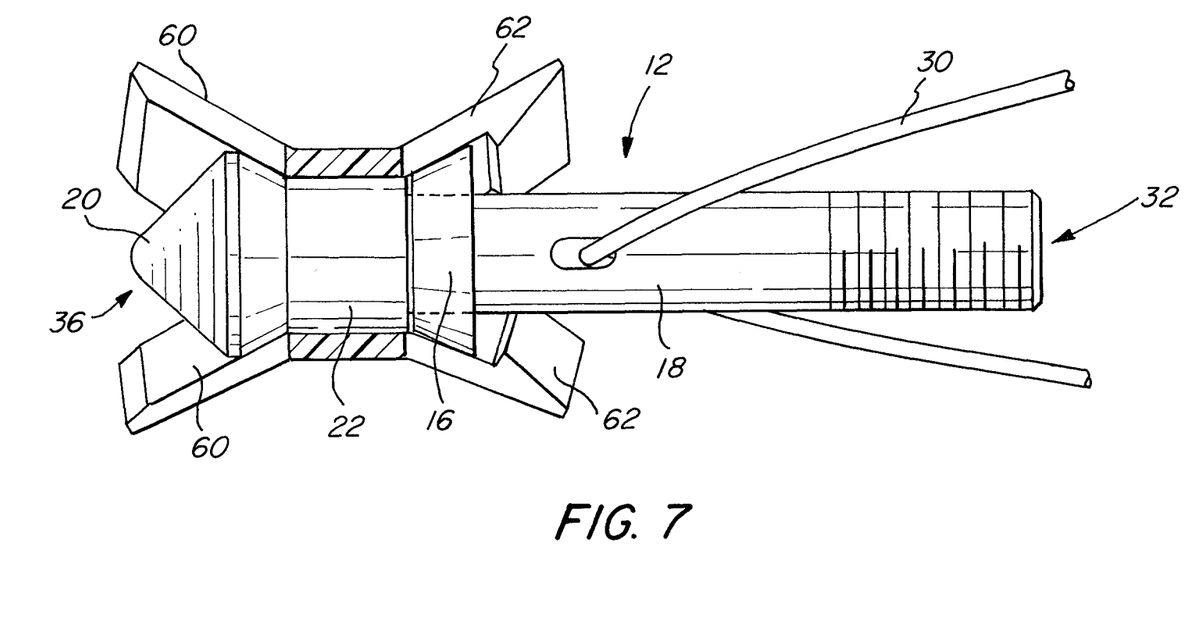
FIG. 7 is a partial side sectional view along line A-A of FIG. 5 of one embodiment of the bone anchor of the present invention.

Sleeve 14, shown in detail in FIGS. 3a-3d, having an internal channel 40, is received over the proximal end 38 of the rivet 12. The diameter 41 of internal channel is larger than the rivet body diameter 24, but is smaller than the rivet head diameter 26, the utility of which will be described below. Provided on the inner surface of sleeve 14 is a distal camming surface 42 and a proximal camming surface 44 which terminates in a shoulder 46. Both the distal 42 and proximal 44 camming surfaces may be tapered to facilitate camming of the sleeve over head 20 and expansion nut 16. Sleeve 14 is also provided with at least one axially-extending slit in its distal end 48 and at least one axially-extending slit in its proximal end 50. Preferably, sleeve 14 has at least two distal axially-extending slits 48 and at least two proximal axially-extending slits 50. More preferably, sleeve 14 has four distal axially-extending slits 48 and four proximal axially-extending slits 50. Slits 48, 50 define a plurality of flexible wall sections 60, 62 and permit the distal and proximal ends, respectively, to be splayed as shown in FIG. 7.

Figure 4A:
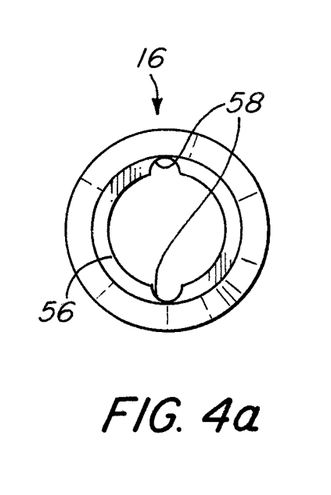
FIG. 4a is a front view of one embodiment of the expansion nut for use with the bone anchor of the present invention.
Figure 4B:
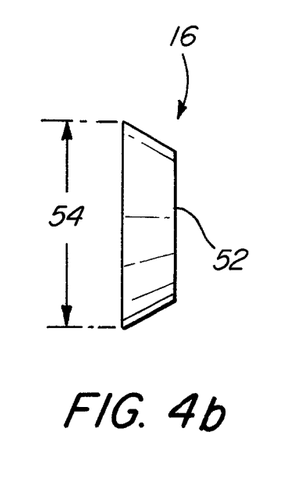
FIG. 4b is a side view of one embodiment of the expansion nut for use with the bone anchor of the present invention.
Figure 5:
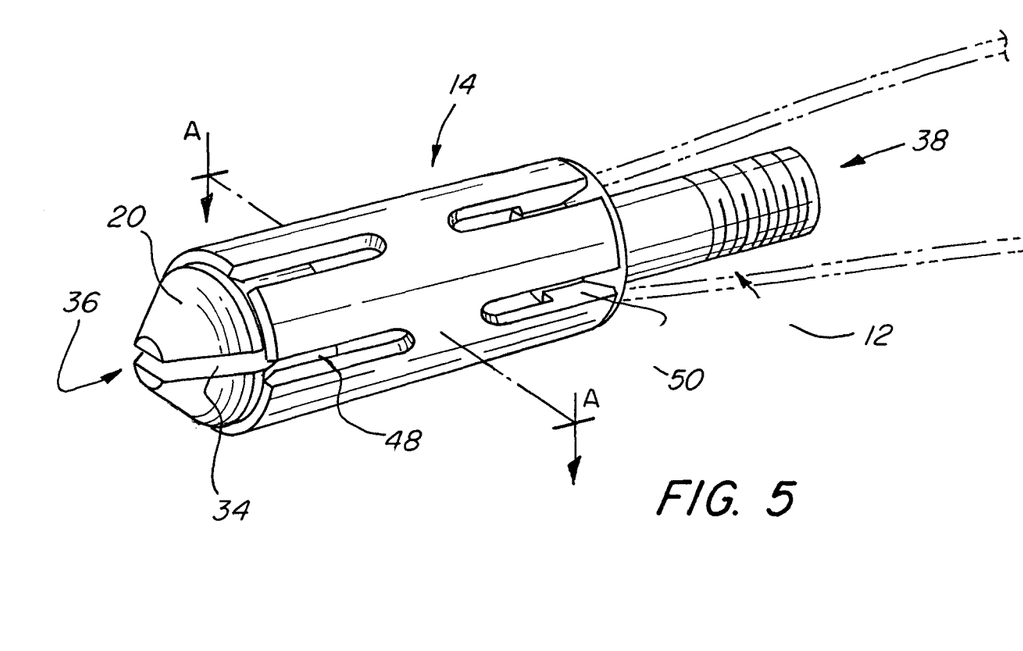
FIG. 5 is a perspective view of one embodiment of the bone anchor of the present invention.

Referring now to FIGS. 4a and 4b, expansion nut 16, having through-hole or channel 56, is received over the proximal end 38 of rivet 12 so that the leading end 52 abuts the proximal end of sleeve 14. Preferably, the leading edge 52 is tapered to facilitate the insertion of the expansion nut 16 between rivet 12 and sleeve 14. The maximum outer diameter 54 of expansion nut 18 is larger than the inner diameter 40 of the sleeve 14, the utility of which will be described below. Because expansion nut 16 fits closely around rivet 12, the through-hole 56 is provided with at least two grooves 58 for accommodating a suture 30.

Figure 6:
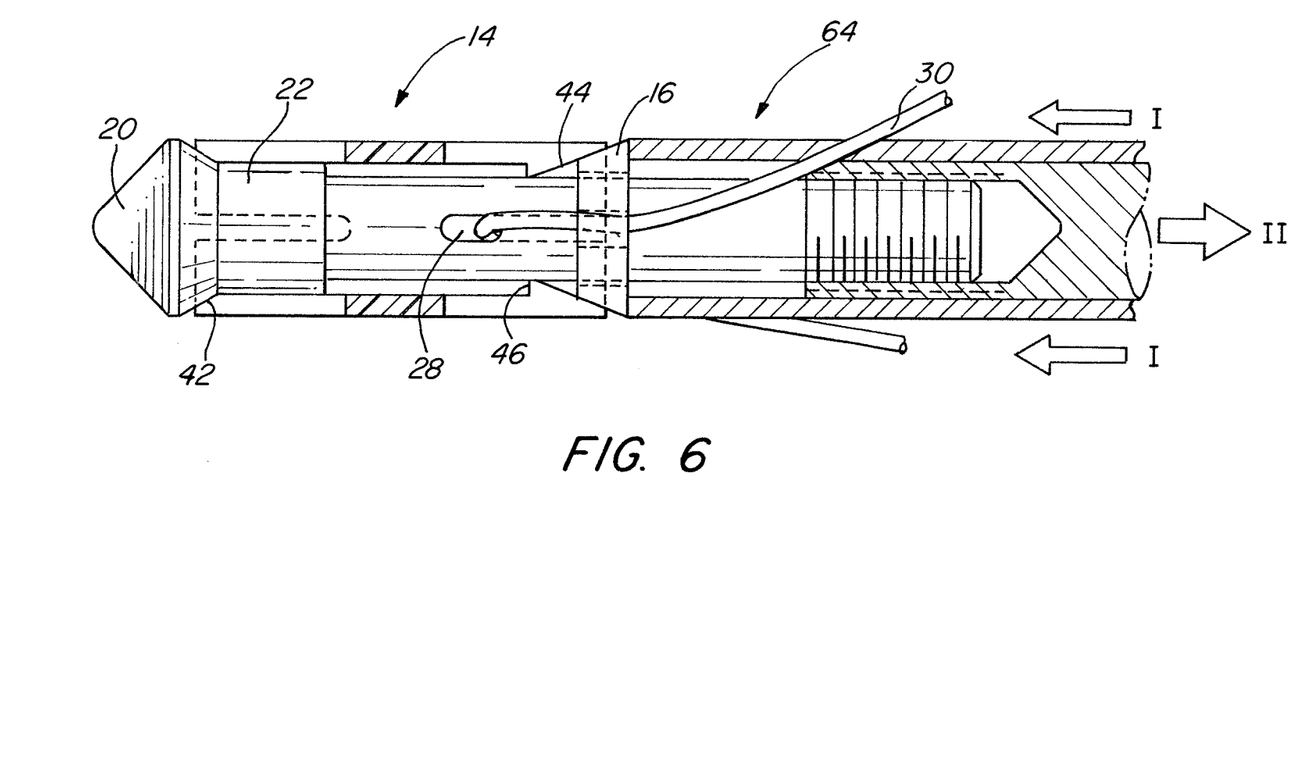
FIG. 6 is a partial side sectional view along line A-A of FIG. 5 of one embodiment of the bone anchor of the present invention.

In operation, a bore or tunnel, having a diameter such that bone anchor 10 fits closely within the opening, is drilled in a bone (not shown) by means known in the art. The bone anchor 10, as assembled in FIG. 6, is then introduced into the bone tunnel and an axial force is applied—either by pulling rivet 12 in a proximal direction (Arrow II), pushing expansion nut in a distal direction (Arrow I), or both—so that the sleeve 14 is caused to cam over rivet head 20 at its distal camming surface 42 and over expansion nut 16 at proximal camming surface 44. As described above, the proximal edge 23 of head 20, the distal camming surface 42, the proximal camming surface 44 and the leading edge 53 of the expansion nut are preferably tapered to facilitate camming of the sleeve 14.

As sleeve 14 cams over head 20 and expansion nut 16, slits 48, 50 splay open and the plurality of flexible wall sections 60, 62 press into the surrounding bone, thus securing the anchor 10 within the tunnel. Notably, sleeve 14 expands open at both ends to create two sets of opposing wall sections 60, 62. These opposing wall sections 60, 62, disposed at either end of the sleeve, are significant in that they provide pull-out resistance superior to anchors that only expand at one end, or have fingers which expand at the midsection of the anchor.

Preferably, the proximal end of sleeve 14 cams over expansion nut 16 until it rests on the distal side of shoulder 46 and abuts collar 22. Shoulder 46 thus provides an indication of when expansion nut 16 has achieved maximum deployment within sleeve 14. In addition, shoulder 46 prevents expansion nut 16 from moving in a proximal direction once the anchor 10 is set. Such proximal movement would allow wall sections 62 to contract, possibly allowing the anchor 10 to become loose within the bone tunnel. Thus, shoulder 46 increases the pullout resistance of the anchor 10.

In one embodiment, the disclosed bone anchor 10 is set with a tool similar to a pop rivet gun (not shown). As illustrated in FIG. 6, in this embodiment, the proximal end of the rivet is screwed into the gun 64 until the proximal end of the expansion nut 16 abuts the gun. The anchor 10 is then inserted into the bone tunnel and the gun applies an axial force in the direction of Arrow I to the rivet 12, while applying an axial force in the direction of Arrows II to the expansion nut 16. Other methods for setting the bone anchor 10 are contemplated.

Figure 8:
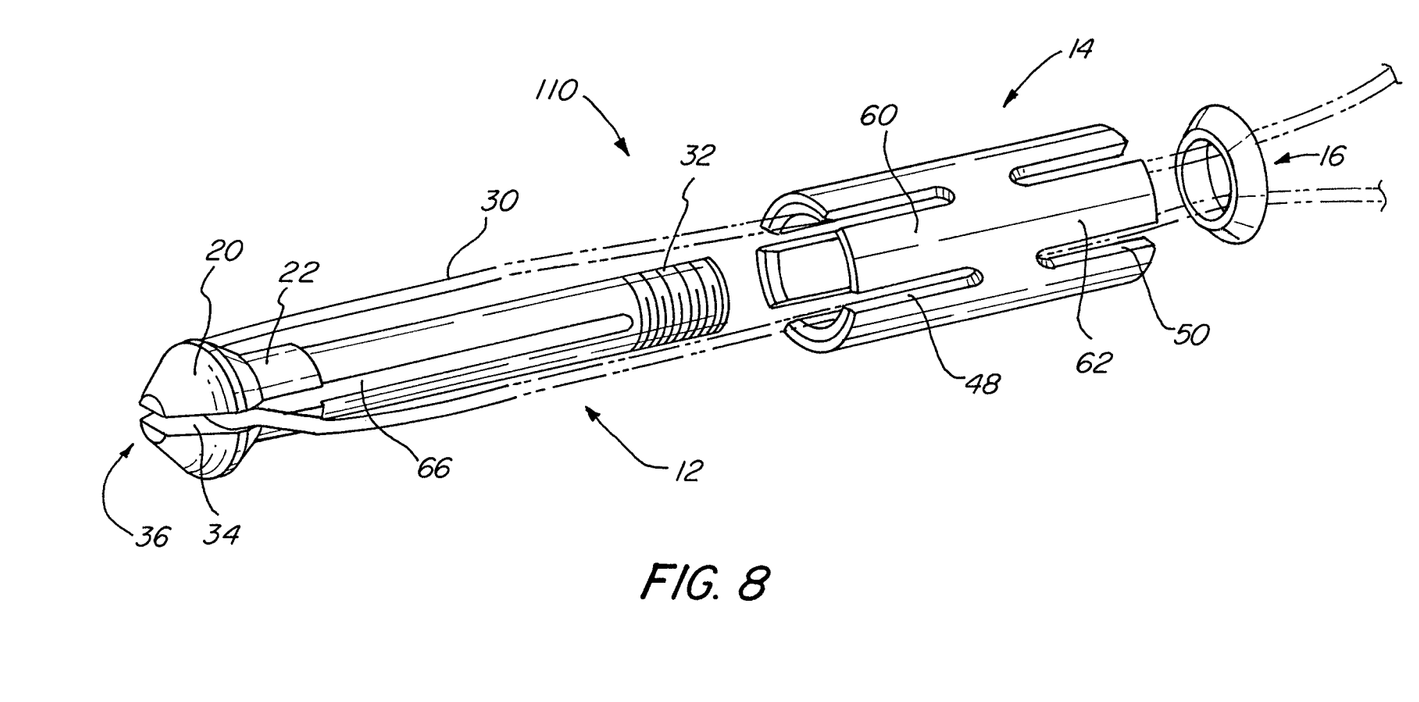
FIG. 8 is an exploded perspective view of one embodiment of the bone anchor of the present invention.
Figure 9:
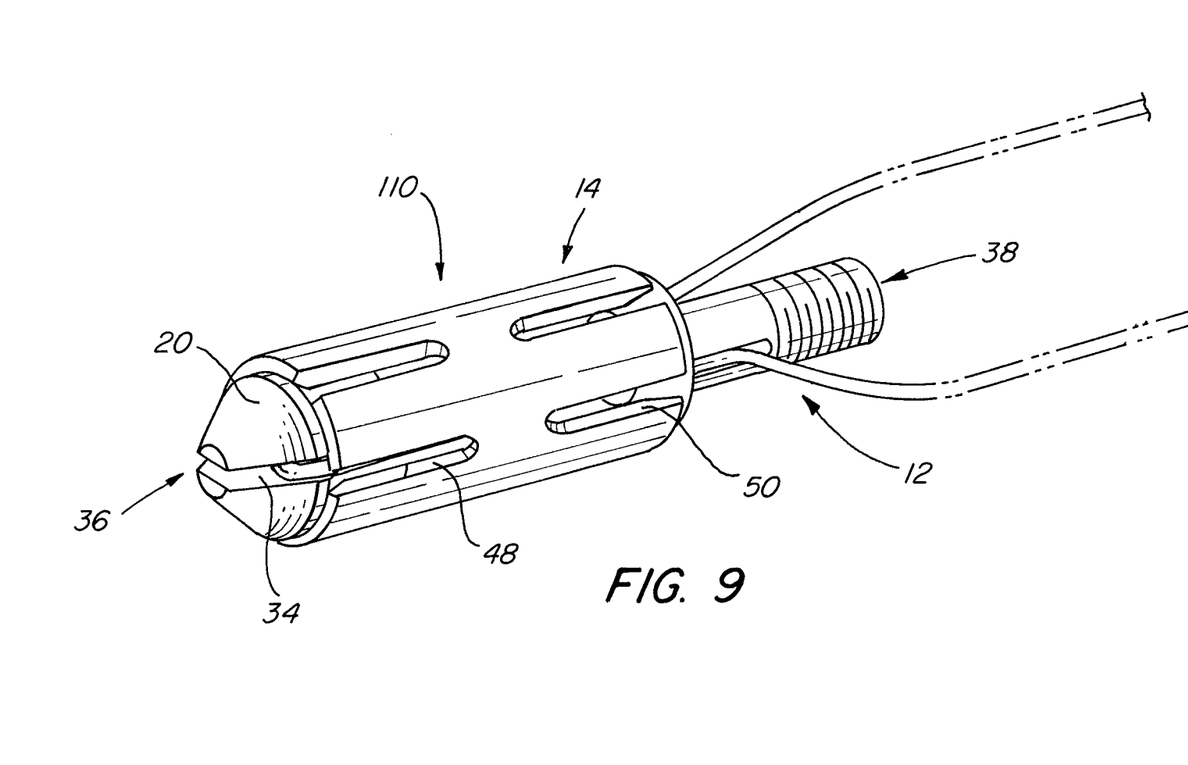
FIG. 9 is a perspective view of one embodiment of the bone anchor of the present invention.
Figure 10:
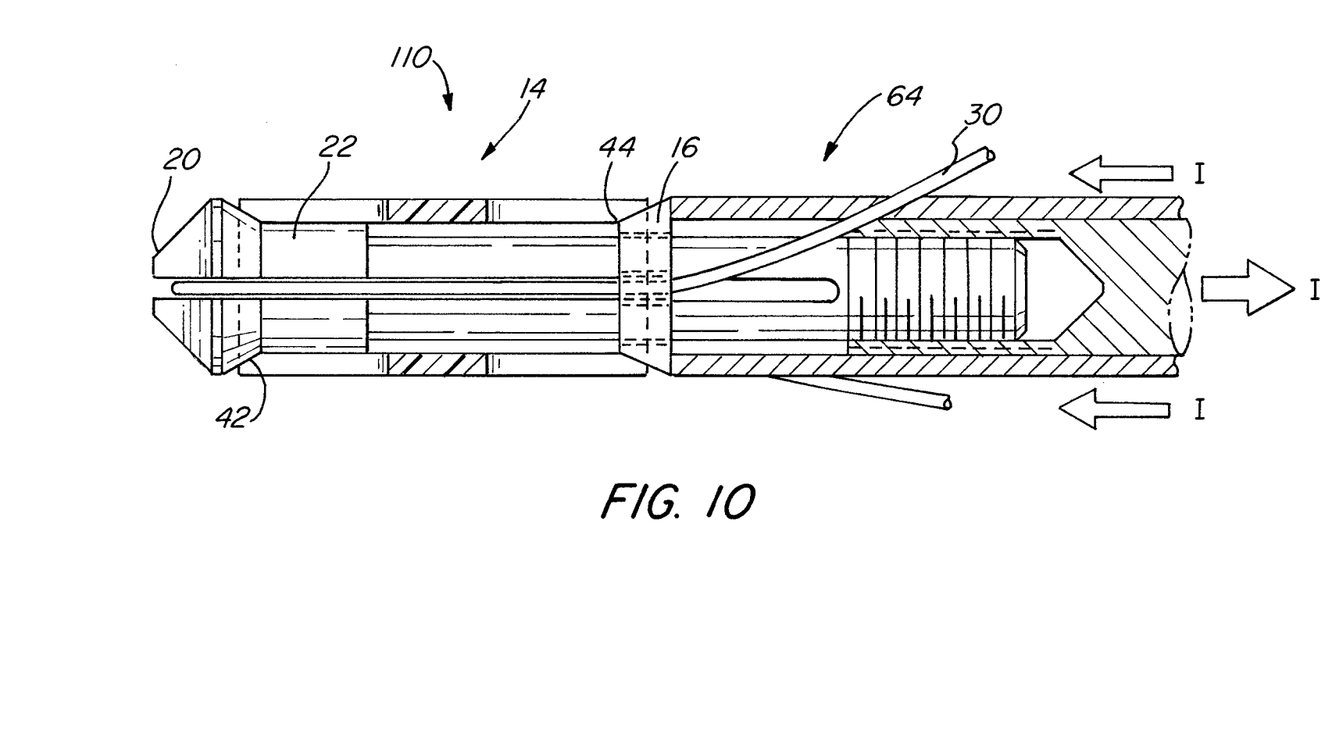
FIG. 10 is a partial side sectional view of one embodiment of the bone anchor of the present invention.

An additional embodiment of bone anchor 110 is shown in FIGS. 8-10. Like elements are labeled the same. In this embodiment, rivet 12 is provided with two elongated grooves 66 on either side, which terminate before threads 32. As shown in FIG. 8, grooves 66 are in line with slot 34 so that when a suture 30 slid into slot 34, it will lie in groove 66 and wrap around the rivet 14. Accordingly, grooves 58 on expansion nut 16 are no longer necessary. In addition, sleeve 14 is provided without shoulder 46. Bone anchor 110 is implanted in the same manner as bone anchor 10.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A bone anchor comprising:
   a rivet having a proximal end and a head distal to an elongate body, said rivet further having a collar disposed proximal of said head;
   a sleeve having an internal channel for slidably receiving the body; and
   an expansion nut having a channel therethrough for slidably receiving said body, proximal of said sleeve;
   the rivet, sleeve and expansion nut being so arranged such that movement of the rivet from a first position to a second position causes the sleeve to cam over the rivet head and said expansion nut until said expansion nut abuts said collar, forcing the sleeve to expand into a wall of a bone hole;
   said sleeve having a shoulder extending radially inward from an inner surface of the internal channel in a region inboard of a proximal end of said sleeve, the shoulder engaging a trailing edge of said expansion nut after expansion of said sleeve.

2. The bone anchor of claim 1 wherein said sleeve further comprises a plurality of axial slits in communication with the internal channel of the sleeve, said plurality of axial slits defining a plurality of flexible wall sections.

3. The bone anchor of claim 2 wherein said plurality of axial slits comprises at least one axial slit at said proximal end of said sleeve, at least one axial slit at a distal end of said sleeve.

4. The bone anchor of claim 2 wherein said plurality of axial slits comprises at least two axial slits at said proximal end of said sleeve and at least two axial slits at a distal end of said sleeve.

5. The bone anchor of claim 2 wherein the inner surface of said sleeve further comprises a distal camming surface for mating with said rivet head and a proximal camming surface for mating with said expansion nut.

6. The bone anchor of claim 5 wherein said sleeve distal camming surface is arranged to telescope over the rivet head and the sleeve proximal camming surface is arranged to telescope over the expansion nut so that when the rivet is moved from a first position to a second position, said plurality of flexible wall sections of said sleeve expand into a wall of a bone hole.

7. The bone anchor of claim 6 wherein said proximal camming surface tapers inwards toward the distal end of said sleeve.

8. The bone anchor of claim 6 wherein said distal camming surface tapers inwards toward the proximal end of said sleeve.

9. The bone anchor of claim 1 wherein said expansion nut has a proximal end and a distal end and wherein said distal end of said expansion nut is tapered.

10. The bone anchor of claim 1 wherein said body further comprises an eyelet and said expansion nut further comprises two grooves on an inner surface thereof for accommodating a suture.

11. The bone anchor of claim 1 wherein said bone anchor is made from a bioabsorbable material.

12. A bone anchor comprising:
    a rivet having a proximal end and a head distal to an elongate body, said rivet further having a collar disposed proximal of said head;
    a hollow sleeve, having at least one axial slit at a proximal end of said sleeve, at least one axial slit at a distal end of said sleeve, and an inner surface;
    said body at least partially slidably received within said sleeve proximal of said head;
    an expansion nut slidably received on said body, proximal of said sleeve, said expansion nut having a leading edge and a trailing edge; and
    said sleeve having a shoulder extending radially inward from the inner surface of said sleeve in a region inboard of the proximal end of said hollow sleeve for engaging the trailing edge of said expansion nut after expansion of said hollow sleeve;
    wherein the rivet, hollow sleeve and expansion nut being so arranged such that movement of the rivet from a first position to a second position causes the sleeve to cam over the rivet head and said expansion nut until said expansion nut abuts said collar, forcing the sleeve to expand into a wall of a bone hole.

13. The bone anchor of claim 12 wherein said expansion nut has a proximal end and a distal end and wherein said distal end of said expansion nut is tapered.

14. The bone anchor of claim 12 wherein the inner surface of said sleeve further comprises a distal camming surface for mating with said rivet head and a proximal camming surface for mating with said expansion nut, said proximal camming surface terminating in said shoulder.

15. The bone anchor of claim 14 wherein said proximal camming surface tapers inwards toward the distal end of said sleeve.

16. The bone anchor of claim 14 wherein said distal camming surface tapers inwards toward the proximal end of said sleeve.

17. The bone anchor of claim 12 wherein said body further comprises an eyelet and said expansion nut further comprises two grooves on an inner surface thereof for accommodating a suture.

18. The bone anchor of claim 12 wherein said bone anchor is made from a bioabsorbable material.

19. The bone anchor of claim 12 wherein said sleeve comprises at least two axial slits at said proximal end of said sleeve and at least two axial slits at said distal end of said sleeve.

20. A method for securing a bone anchor in a bone tunnel comprising the steps of:
providing a tunnel in a bone;
placing a bone anchor in said tunnel, the bone anchor having:
a rivet having a proximal end and a head distal to an elongate body, said rivet further having a collar disposed proximal of said head;
a hollow sleeve adapted to receive said body, having a proximal end, a distal end, and an inner surface; and
an expansion nut slidably received on said body, proximal of said sleeve;
said sleeve further having at least one axial slit at said proximal end of said sleeve, at least one axial slit at said distal end of said sleeve, and a shoulder extending radially inward from the inner surface of said sleeve in a region inboard of the proximal end of said sleeve, the shoulder engaging a trailing edge of said expansion nut;
moving either the rivet in a proximal direction or the expansion nut in a distal direction so that the sleeve cams over the rivet head and expansion nut until said expansion nut rests on the distal side of said shoulder and abuts said collar, causing said sleeve to expand into said bone tunnel at said at least one axial slit at the proximal end of said sleeve and said at least one axial slit at the distal end of said sleeve.

21. The method of claim 20 wherein said expansion nut has a proximal end and a distal end and wherein said distal end of said expansion nut is tapered.

22. The method of claim 20 wherein the inner surface of said sleeve further comprises a distal camming surface for mating with said rivet head and a proximal camming surface for mating with said expansion nut, said proximal camming surface terminating in said shoulder.

23. The method of claim 22 wherein said proximal camming surface tapers inwards toward the distal end of said sleeve.

24. The method of claim 22 wherein said distal camming surface tapers inwards toward the proximal end of said sleeve.

25. The method of claim 20 wherein said body further comprises an eyelet and said expansion nut further comprises two grooves on an inner surface thereof for accommodating a suture.

26. The method of claim 20 wherein said bone anchor is made from a bioabsorbable material.

27. The method of claim 20 wherein said sleeve comprises at least two axial slits at said proximal end of said sleeve and at least two axial slits at said distal end of said sleeve.

28. A bone anchor comprising:
a rivet having a proximal end and a head distal to an elongate body, said rivet further having a collar disposed proximal of said head;
a sleeve having an internal channel for slidably receiving the body; and
an expansion nut having a channel therethrough for slidably receiving said body;
said sleeve further having a shoulder extending radially inward from an inner surface of the internal channel inboard of a proximal end of the sleeve for engaging a trailing edge of said expansion nut;
the sleeve being disposed proximally of the rivet head and the expansion nut being disposed proximally of the sleeve along the body such that movement of the rivet from a first position to a second position causes the sleeve to cam over the rivet head and expansion nut until said expansion nut engages said shoulder and said collar abuts said expansion nut, forcing the sleeve to expand into a wall of a bone hole.

29. The bone anchor of claim 28 wherein said sleeve further comprises a plurality of axial slits in communication with the internal channel of the sleeve, said plurality of axial slits defining a plurality of flexible wall sections.

30. The bone anchor of claim 29 wherein said plurality of axial slits comprises at least one axial slit at said proximal end of said sleeve, at least one axial slit at a distal end of said sleeve.

31. The bone anchor of claim 29 wherein said plurality of axial slits comprises at least two axial slits at said proximal end of said sleeve and at least two axial slits at said distal end of said sleeve.

32. The bone anchor of claim 29 wherein the inner surface of said sleeve further comprises a distal camming surface for mating with said rivet head and a proximal camming surface for mating with said expansion nut, said proximal camming surface terminating in said shoulder.

33. The bone anchor of claim 32 wherein said sleeve distal camming surface is arranged to telescope over the rivet head and the sleeve proximal camming surface is arranged to telescope over the expansion nut so that when the rivet is moved from a first position to a second position, said plurality of flexible wall sections of said sleeve expand into a wall of a bone hole.

34. The bone anchor of claim 32 wherein said proximal camming surface tapers inwards toward a distal end of said sleeve.

35. The bone anchor of claim 32 wherein said distal camming surface tapers inwards toward a said proximal end of said sleeve.

36. The bone anchor of claim 28 wherein said expansion nut has a proximal end and a distal end and wherein said distal end of said expansion nut is tapered.

37. The bone anchor of claim 28 wherein said body further comprises an eyelet and said expansion nut further comprises two grooves on an inner surface thereof for accommodating a suture.

38. The bone anchor of claim 28 wherein said bone anchor is made from a bioabsorbable material.

39. A bone anchor comprising:
a rivet having a proximal end and a head distal to an elongate body having two elongate grooves, said rivet further having a collar disposed proximal of said head;
a hollow sleeve, having at least one axial slit at a proximal end, at least one axial slit at a distal end, and an inner surface;
said body at least partially slidably received within said sleeve proximal of said head;
an expansion nut slidably received on said body, proximal of said sleeve; said head further having a slot for accommodating a suture; and
said sleeve having a shoulder extending radially inward from the inner surface of said hollow sleeve in a region inboard of the proximal end of said hollow sleeve for engaging a trailing edge of said expansion nut;
wherein the rivet, sleeve and expansion nut being so arranged such that movement of the rivet from a first position to a second position causes the sleeve to cam over the rivet head and said expansion nut until said expansion nut abuts said collar, forcing the sleeve to expand into a wall of a bone hole.

40. The bone anchor of claim 39 wherein said two elongate grooves are in line with said slot.

41. The bone anchor of claim 39 wherein said expansion nut has a proximal end and a distal end and wherein said distal end of said expansion nut is tapered.

42. The bone anchor of claim 39 wherein the inner surface of said sleeve further comprises a distal camming surface for mating with said rivet head and a proximal camming surface for mating with said expansion nut, said proximal camming surface terminating in a shoulder.

43. The bone anchor of claim 42 wherein said proximal camming surface tapers inwards toward the distal end of said sleeve.

44. The bone anchor of claim 42 wherein said distal camming surface tapers inwards toward the proximal end of said sleeve.

45. The bone anchor of claim 39 wherein said sleeve comprises at least two axial slits at said proximal end of said sleeve and at least two axial slits at said distal end of said sleeve.

* * * * *

UNITED STATES PATENT AND TRADEMARK OFFICE
CERTIFICATE OF CORRECTION

PATENT NO.       : 8,906,060 B2
APPLICATION NO.  : 12/491037
DATED            : December 9, 2014
INVENTOR(S)      : Rickey Hart It is certified that error appears in the above-identified patent and that said Letters Patent is hereby corrected as shown below:

On the Title Page

Item (73) Assignee should read: Karl Storz GmbH & Co. KG, (DE)

Signed and Sealed this
Twelfth Day of May, 2015

Michelle K. Lee
*Director of the United States Patent and Trademark Office*